(12) United States Patent
Matschenko et al.

(10) Patent No.: US 7,381,564 B2
(45) Date of Patent: Jun. 3, 2008

(54) METHOD OF CALIBRATING THE ZERO POINT OF AN APPARATUS USED TO DETERMINE A QUANTITY OF SILICA USING A COLORIMETRIC METHOD

(75) Inventors: Alec Matschenko, Xonrupt-Longemer (FR); Fabien Lemaitre, Neuilly-sur-Marne (FR); Rachid Qarbi, Autie (FR)

(73) Assignee: Hach Sas, Noisy-le-Grand (FR)

( * ) Notice: Subject to any disclaimer, the term of this patent is extended or adjusted under 35 U.S.C. 154(b) by 0 days.

(21) Appl. No.: 10/529,754

(22) PCT Filed: Oct. 3, 2003

(86) PCT No.: PCT/FR03/02917

§ 371 (c)(1),
(2), (4) Date: Oct. 11, 2006

(87) PCT Pub. No.: WO2004/031751

PCT Pub. Date: Apr. 15, 2004

(65) Prior Publication Data

US 2007/0037289 A1    Feb. 15, 2007

(30) Foreign Application Priority Data

Oct. 4, 2002  (FR) ................... 02 12305

(51) Int. Cl.
*G01N 33/38* (2006.01)
*G01N 21/75* (2006.01)
*G01N 31/00* (2006.01)

(52) U.S. Cl. .................. 436/19; 436/8; 436/164; 436/166

(58) Field of Classification Search ............... 436/8, 436/19, 164, 166
See application file for complete search history.

(56) References Cited

U.S. PATENT DOCUMENTS

| | | | | |
|---|---|---|---|---|
| 2,950,396 A | * | 8/1960 | Schneider, Jr. | 422/81 |
| 3,015,544 A | | 1/1962 | Schneider, Jr. | |
| 3,030,192 A | | 4/1962 | Schneider, Jr. | |
| 3,773,423 A | * | 11/1973 | Hach | 356/410 |
| 5,230,863 A | * | 7/1993 | Salpeter | 422/67 |
| 5,550,053 A | * | 8/1996 | Salpeter | 436/8 |
| 2005/0208669 A1 | * | 9/2005 | Kaneko et al. | 436/72 |

FOREIGN PATENT DOCUMENTS

| | | |
|---|---|---|
| GB | 793 792 | 4/1958 |
| JP | 04 109166 | 4/1992 |

OTHER PUBLICATIONS

Patent Abstracts of Japan, vol. 016, No. 355, P-1394, Jul. 30, 1992.

* cited by examiner

*Primary Examiner*—Maureen M. Wallenhorst
(74) *Attorney, Agent, or Firm*—Jacobson Holman PLLC

(57) ABSTRACT

A method of calibrating the zero point of an apparatus which is used to determine the quantity of silica contained in a silica solution sample to be analysed, using a colorometric method. The colorometric method used by the apparatus consists of successively introducing the following components into the sample: a molybdate solution, a developer and a reagent. In order to determine the zero point, the developer is first introduced into the sample of silica solution to be analyzed, a first measurement is taken, followed by addition of the molybdate solution and the reducing agent to the sample, where a second measurement is take and the zero point is calculated.

7 Claims, No Drawings

METHOD OF CALIBRATING THE ZERO POINT OF AN APPARATUS USED TO DETERMINE A QUANTITY OF SILICA USING A COLORIMETRIC METHOD

This is a nationalization of PCT/FR03/002917 filed Oct. 3, 2003 and published in French.

The present invention relates to a method for calibrating the zero point of an apparatus that determines an amount of silica using a colourimetric method.

It will be recalled that the measurement of silica dissolved in low concentration is extremely important, especially in the field of electrical production and the semiconductor industry.

The silica that is present in the water may precipitate during the expansion of the water vapour over the turbine of a power station or, in specific phases of the treatment of the discs or wafers, during the production of the semiconductors.

On the other hand, the presence of silica in the demineralised waters may also serve as an indicator that the deionisation resins have stopped working. This silica presence invariably precedes the release of the monovalent ions such as, in particular, the sodium and chloride ions.

This amount of silica in solution is measured using a colourimetric method: a complex that is specific to the silica to be measured and that develops its own individual colour is provided for this purpose.

A light emitted into a solution of this type is absorbed by the provided complex proportionally to its concentration in accordance with the Beer-Lambert law:

$$I = I_0 \exp(-kLC) \quad (1)$$

in which:
- I is the measurement of the amount of light received through the solution;
- $I_0$ is the amount of light emitted into the solution;
- L is the length of the optical path crossed by the light;
- C is the concentration of the provided complex; and
- K is a constant linked to the measuring device and to the molecular extinction coefficient of the analysed solution.

The Beer-Lambert law expresses a correlation between the concentration and an absorption measurement of an amount of light. In other words, it expresses the fact that the concentration is connected to an absorption measurement of an amount of light by means of a linear law.

$$C = C_0 + K \cdot \log(I_0/I) \quad (2)$$

in which:
- $C_0$ is referred to as the zero point of the measurement;
- K is the gradient of the measurement;
- $I_0$ is the intensity measurement of the emitted light; and
- I is the measurement of the light intensity received through the solution.

It will be noted from the above equation (2) that two methods are possible for determining the coefficients of the linear equation connecting the concentration to the light absorption optical measurement:

Determining the light absorption of a solution without silica containing the necessary reagents for the measurement, in order to determine the zero point, then the light absorption by a highly concentrated silica solution within the measurement range of the apparatus, in order to determine the gradient.

Determining the light absorption of two solutions having a known silica concentration.

Both of these methods require the initial silica concentration of the water used to prepare the reference solutions to be known in order to calculate the zero point and gradient coefficients. However, this concentration is unknown. Nevertheless, the following two linear equations (3) and (4) should allow the silica measurement to be calibrated:

$$C_1 + X = C_0 + K \cdot \log(I_0/I_1) \quad (3)$$

$$C_2 + X = C_0 + K \cdot \log(I_0/I_2) \quad (4)$$

in which:
- $I_0$ is the measurement of the amount of light as a function of the solution that is present in the cell;
- $I_1$ is the known concentration of the reference solution 1;
- $I_2$ is the known concentration of the reference solution 2; and
- X is the unknown concentration of the water for preparing the solutions 1 and 2 having a low silica concentration.

These two linear equations (3) and (4) comprise three unknown elements $C_0$, K and X and can therefore not be solved.

It is therefore not possible to know in a simple manner the real gradient and zero point of the measurement from the simple preparation of prepared solutions, as explained above.

Moreover, the other simple known methods for measuring a solution having a low silica concentration do not provide an absolute measurement of the silica concentration and all have this same drawback.

Among the methods used for calibrating the silica measurement, the following two may be cited in particular.

According to the first method, the silica residue in the dilution water may be measured by mass spectrometry (ICP-MS: Inductively Coupled Plasma-Mass Spectrometry): this method is difficult to implement and does not seem to be economically usable in industrial on-line measurement.

According to a second method, the gradient is determined by measuring a high-concentration solution for which the error in the preparation of this solution and the error in the zero point of the measurement will be negligible relative to its concentration. For this purpose, two reference solutions, of which the more concentrated solution is obtained by pre-concentrating the first solution by a factor N of at least 20, are produced by heating and evaporating said first solution by means of controlled microwaves. The two solutions thus have concentrations X and N.X, wherein N is the pre-concentration factor that is in the ratio of the volumes before and after evaporation. The linear equations (5) and (6) are thus obtained:

$$X = C_0 + K \cdot \log(I_0/I_1) \quad (5)$$

$$N \cdot X = C_0 + K \cdot \log(I_0/I_2) \quad (6)$$

in which the parameters have the same values as in the equations (3) and (4).

This method allows the linear equations (5) and (6) to be solved and the zero point of the apparatus to be deduced therefrom, provided that K is known. However, it has the drawback of having an extremely long response time (the pre-concentration procedure has to be slow and controlled) and it is also inapplicable in an industrial setting and in process control.

A further aim of the present invention is to provide a method for calibrating the zero point of an apparatus that determines an amount of silica using a colourimetric method, allowing this calibration to be carried out within an acceptable period.

A further aim of the invention is to provide such a method that is simple to implement.

These aims and others that will subsequently become apparent are achieved by a method for calibrating the zero point of an apparatus that determines the amount of silica contained in a silica solution sample to be analysed using a colourimetric method consisting in successively introducing into this sample a molybdate solution, a developer and a reagent, said method being characterised, according to the present invention, by the fact that the developer, then the molybdate solution and finally the reducing agent are successively introduced into a sample of the silica solution to be analysed.

In an apparatus for analysing the silica contained in a solution, the sample to be analysed circulates in a rapid loop, allowing rapid renewal of the sample. The flow rate is adjusted by means of a needle valve. At the start of the analysis, the sample is introduced into the measuring cell by means of the electromagnetic valve. A molybdate solution, which reacts with the silica contained in the sample, is then added: a silicomolybdic complex is thus obtained. The reaction time is relatively long (around 300 sec).

A developer, such as oxalic acid, is then added in order to prevent phosphate interferences and to develop and intensify the colour of the silicomolybdic complex.

This silicomolybdic complex is then reduced to a blue molybdenum complex by means of ferrous ions.

A light absorption photometric measurement is carried out at the end of the reaction.

The silica dissolved in solution is in the form of salicylic acid or various types of silicates. The acidic molybdate thus reacts with the silica in solution to form a silicomolybdic complex that is yellow in colour and may be detected by the light absorption measurement in order to detect a concentration of some mg/l [ppm: part per million]. After reduction, the yellow compound is transformed into a complex that is blue in colour and allows a more sensitive detection of the silica concentration at the level of the µg/l [ppb: part per billion].

In order to calibrate the zero point of an apparatus of this type using the above analysis method, oxalic acid (developer), then the molybdate solution and finally the reducing agent are introduced into a solution sample to be analysed.

The method in accordance with the present invention thus:
- allows the light absorption due to the colouration and to the possible turbidity of the reagents to be compensated;
- allows the light absorption due to the blue silicomolybdic complex formed from the silica contained in the molybdate solution to be compensated; and
- prevents the silica contained in the water at the moment of the preparation serving to calibrate the zero point from reacting and forming the blue silicomolybdic complex.

The tests that were carried out revealed that the light absorption measurement I remains unchanged to within 1/1000 for solutions comprising between 0.5 µg/l and 200 µg/l of dissolved silica. They demonstrate that the reaction resulting in the silicomolybdic compound cannot take place.

This reference measurement, which allows the zero point of the apparatus to be calculated and which does not depend on the concentration of the dissolved silica solution on which it is carried out, was then correlated with the pre-concentration method described above: the measurements obtained using the two methods are identical.

The aim of the following example for determining the zero point is to allow a person skilled in the art to obtain a better understanding of the implementation of the method in accordance with the present invention.

EXAMPLE

A sample that was present in an overflow tank was introduced into a measuring cell, the volume of which was approximately 8.5 ml. 250 µl of a solution of 40 g of oxalic acid 2H20 were then added.

The mixture thus obtained was continuously stirred in order to homogenise it as quickly as possible: the measuring cell, which was made of a heat-conducting material, was maintained at a constant temperature of 25° C.

Around two minutes after the introduction of the oxalic acid, a first absorption measurement of the light in this cell was carried out: this measurement, $I_0$, was the intensity measurement of the light emitted in the Beer-Lambert formula recalled above.

250 µl of a molybdate solution, the composition of which for 1 liter was:

| | |
|---|---|
| Sodium molybdate, 4H2O | 35 g |
| Sodium hydrogen sulphate, 1H2O | 80 g |
| Sodium hydrogen sulphate, anhydrous | 70 g |
| Concentrated sulphuric acid | 25 g | were then introduced.

After one minute, a reducing agent, the composition of which for 1 liter was:

| | |
|---|---|
| Concentrated sulphuric acid | 12.5 g |
| Mohr's salt (ammonium ferrosulphate, 6H2O) | 20 g | was then added.

A second light absorption measurement I was carried out one minute after the addition of the reducing agent.

By applying the Beer-Lambert formula, which expresses a proportionality between the silica concentration in the sample and an absorption measurement of an amount of light, the zero point of the measuring apparatus was determined.

The zero point may be calibrated using the same method, but with different reagents used for measuring the silica by means of colourimetry. Thus, in the colourimetric method using a molybdate, a mixture of citrates, then a reducing agent such as amino-naphthol sulphonic acid, the zero point in accordance with the present invention will be determined by introducing the mixture of citrates, the molybdate, then the reducing agent into the sample.

The invention claimed is:
1. A method for calibrating the zero point of an apparatus that determines the amount of silica contained in a sample solution by using a colorimetric method having the successive steps of adding a molybdate solution, a developer solution, and a reducing agent to the sample, followed by light absorption measurement, said zero point calibration method comprising the following steps:
- a) obtaining a sample to be analyzed;
- b) introducing into said sample the developer solution;
- c) obtaining a first absorption measurement of said sample;
- d) introducing into said sample the molybdate solution;
- e) introducing into said sample a reducing agent;
- f) obtaining a second absorption measurement of said sample; and
- g) calculating the zero point for the apparatus using the first and second absorption measurements.

2. The method according to claim 1, wherein said developer solution comprises a solution containing an organic acid.

3. The method of claim 2, wherein said organic acid is oxalic acid.

4. The method of claim 2, wherein said organic acid comprises citric acid or a mixture of citrates.

5. The method of claim 1, wherein said molybdate solution comprises a mixture of sodium molybdate, sodium hydrogen sulfate, and sulfuric acid.

6. The method of claim 1, wherein said reducing agent comprises sulfuric acid and ammonium ferrosulfate.

7. The method of claim 1, wherein said reducing agent comprises amino-napthol sulfonic acid.

* * * * *